United States Patent
Kim et al.

(10) Patent No.: US 12,252,421 B2
(45) Date of Patent: Mar. 18, 2025

(54) SYSTEM AND METHOD FOR TREATING WASTE WATER

(71) Applicant: SK Innovation Co., Ltd., Seoul (KR)

(72) Inventors: Tae Wan Kim, Daejeon (KR); Yoon Hyuk Jang, Daejeon (KR); Min Youb Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 585 days.

(21) Appl. No.: 17/564,328

(22) Filed: Dec. 29, 2021

(65) Prior Publication Data
US 2022/0204371 A1 Jun. 30, 2022

(30) Foreign Application Priority Data
Dec. 30, 2020 (KR) .......... 10-2020-0187253

(51) Int. Cl.
| C02F 1/78 | (2023.01) |
| C02F 1/00 | (2023.01) |
| G01N 33/18 | (2006.01) |
| C02F 101/30 | (2006.01) |

(52) U.S. Cl.
CPC ........... *C02F 1/78* (2013.01); *C02F 1/008* (2013.01); *G01N 33/1806* (2013.01); *C02F 2101/30* (2013.01); *C02F 2201/782* (2013.01); *C02F 2209/08* (2013.01); *C02F 2209/23* (2013.01)

(58) Field of Classification Search
CPC ........ C02F 1/78; C02F 1/008; C02F 2101/30; C02F 2201/782; C02F 2209/08; C02F 2209/23; C02F 2209/006; G01N 33/1806
See application file for complete search history.

(56) References Cited

U.S. PATENT DOCUMENTS

2019/0248689 A1   8/2019   Miller et al.

FOREIGN PATENT DOCUMENTS

| CN | 111257395 A | * | 6/2020 |
| JP | 200417003 A | | 1/2004 |
| JP | 3537995 B2 | | 6/2004 |
| WO | WO-2020166074 A1 | * | 8/2020 |

* cited by examiner

*Primary Examiner* — Waqaas Ali
(74) *Attorney, Agent, or Firm* — The Webb Law Firm

(57) ABSTRACT

Provided is a wastewater treatment method including measuring a chemical oxygen demand (COD) of wastewater containing organic matter in real time, calculating the amount of ozone associated with a concentration of the organic matter using the measured COD value, and controlling a production of ozone of an ozone generator based on the calculated amount of ozone. The present invention provides a wastewater treatment method and system for adjusting the production of ozone used as an oxidizing agent for decomposing organic matter in wastewater in association with a load of organic matter in wastewater to be oxidized.

12 Claims, 4 Drawing Sheets

[FIG. 1]
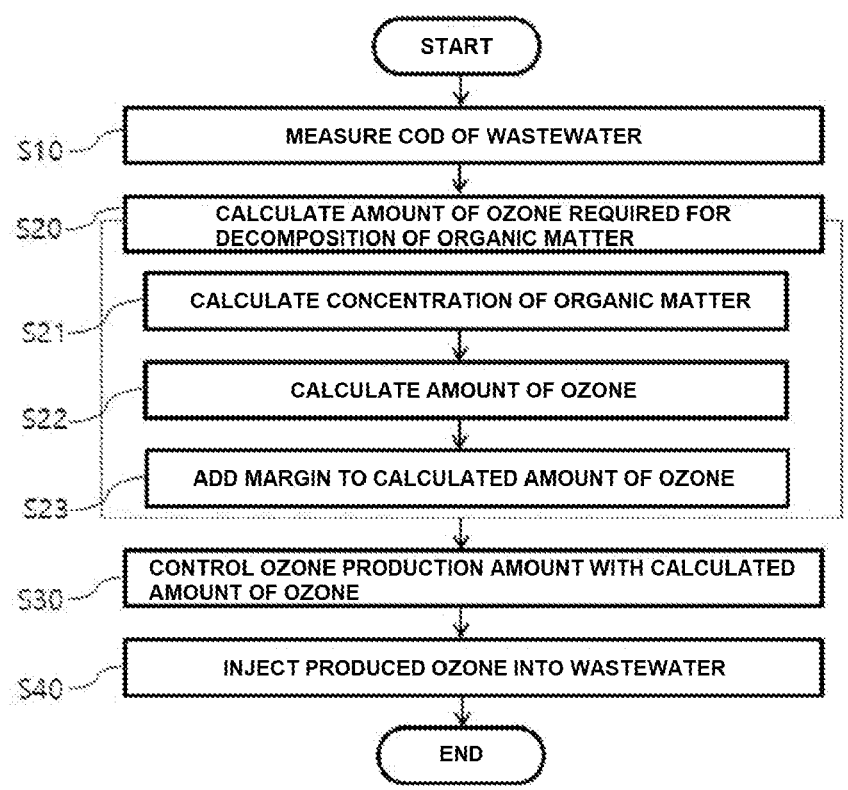

[FIG. 2]
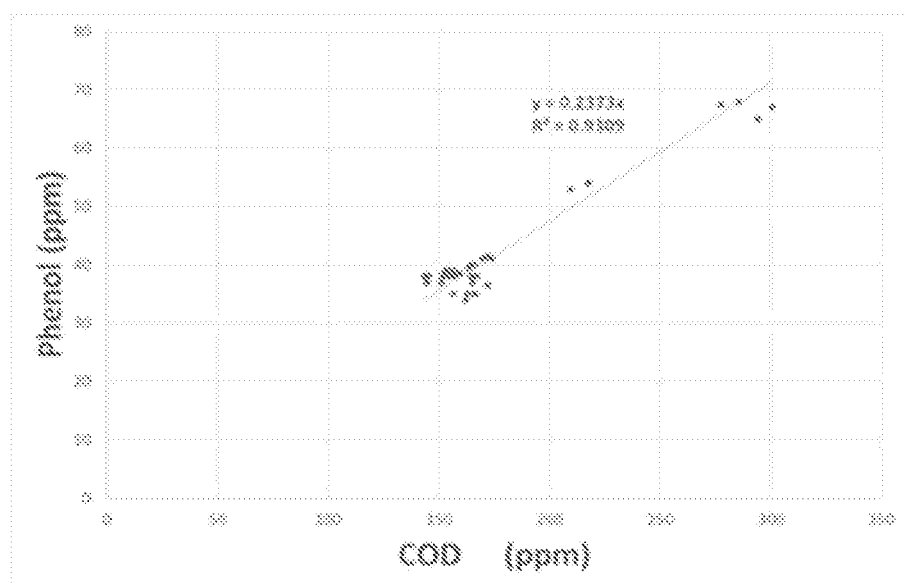

[FIG. 3]
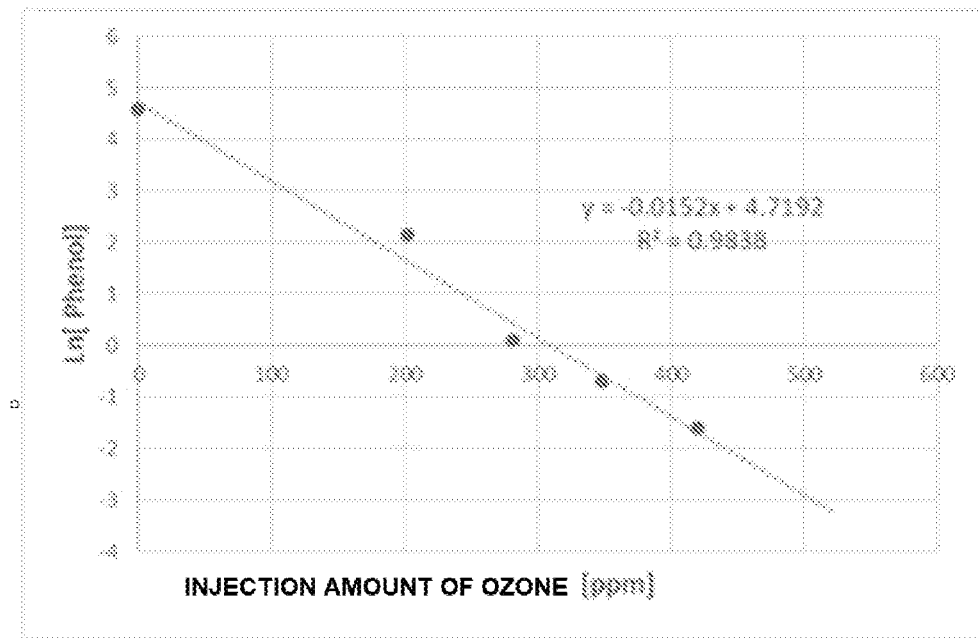

【FIG. 4】
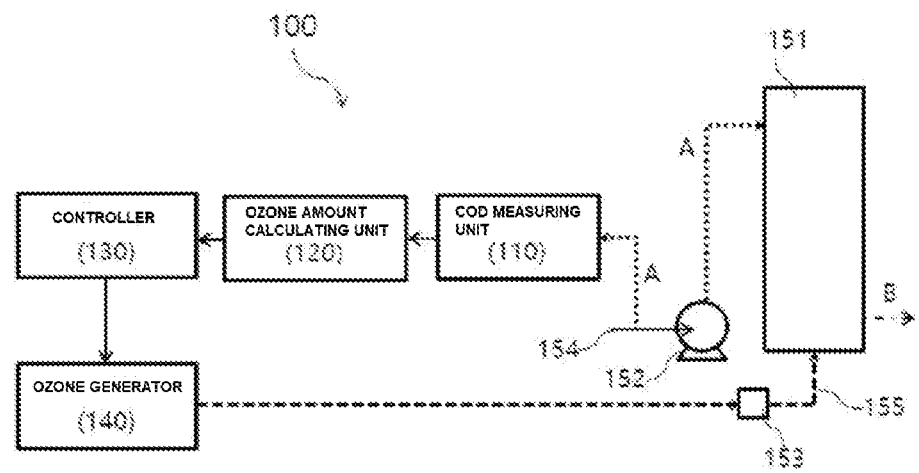

SYSTEM AND METHOD FOR TREATING WASTE WATER

CROSS-REFERENCE TO RELATED APPLICATION

This application claims priority to Korean Patent Application No. 10-2020-0187253 filed Dec. 30, 2020, the disclosure of which is hereby incorporated by reference in its entirety.

BACKGROUND OF THE INVENTION

Field of the Invention

The present invention relates to a wastewater treatment system and method, and more particularly, to a wastewater treatment system and method for regulating an emission rate of ozone in association with an organic load in wastewater.

Description of the Related Art

As environmental pollution has intensified and social interest in eco-friendliness has increased, legal water quality management standards have been strengthened. For example, a discharge standard of a water quality affecting area was changed from chemical oxygen demand (COD) 40 ppm to total organic carbon (TOC) 25 ppm.

An advanced oxidation process (AOP) is attracting attention for oxidation of organic matter in wastewater. Ozone, UV, electricity, and catalyst-based AOPs have been introduced, among which ozone-based technology has been widely used commercially.

Ozone has a very high electron affinity, so it acts on unsaturated bonds or aromatic rings of various kinds of organic matter and organometallic functional groups to oxidatively decompose organic matter or organometals to produce low molecular substances, and thus, ozone is used for oxidation of organic matter.

Ozone is used in a small amount in water purification, but in wastewater treatment, an excessive amount of ozone is generally injected for a stable wastewater treatment. Therefore, in order to economically treat wastewater and prevent environmental pollution that may be caused by excess ozone not used for oxidation of organic matter, a wastewater treatment method for reducing an occurrence of excess ozone is required.

SUMMARY OF THE INVENTION

Technical Problem

An object of the present invention is to provide a wastewater treatment method and system for adjusting the production of ozone used as an oxidizing agent for decomposing organic matter in wastewater in association with a load of organic matter in wastewater to be oxidized.

Technical Solution

According to an embodiment of the present invention, a wastewater treatment method includes: measuring a chemical oxygen demand (COD) of wastewater containing organic matter in real time; calculating the amount of ozone associated with a concentration of the organic matter using the measured COD value; and controlling the production of ozone of an ozone generator based on the calculated amount of ozone.

In addition, the calculating of the amount of ozone may include calculating the concentration of the organic matter contained in the wastewater through a correlation expression between the measured COD value and the concentration of the organic matter contained in the wastewater, which is previously derived to predict the concentration of the organic matter in the wastewater based on the COD value of the wastewater.

In addition, the correlation expression may calculate the concentration of organic matter in the wastewater by multiplying the COD value by a previously derived correlation ratio.

In addition, in the calculating of the amount of ozone, the amount of ozone used for decomposing the organic matter contained in the wastewater to a target concentration or less may be calculated.

In addition, the calculating of the amount of ozone may further include: calculating the amount of ozone through an ozone production formula previously derived to calculate the amount of ozone required for decomposition of the organic matter compared with the concentration of the organic matter, the ozone production formula calculating the amount of ozone compared with the concentration of the organic matter calculated in the calculating of the concentration of the organic matter contained in the wastewater.

In addition, the ozone production formula may calculate the amount of ozone required for decomposition of the organic matter contained in the wastewater by multiplying the calculated concentration of the organic matter by a comparison value of the amount of ozone required for decomposition of the organic matter contained in the wastewater to a target concentration with respect to the concentration of the organic matter.

In addition, the calculating of the amount of ozone may further include adding a margin from the amount of ozone calculated through the ozone production formula.

According to an embodiment of the present invention, a wastewater treatment system includes: a chemical oxygen demand (COD) measuring unit measuring a COD of wastewater containing organic matter in real time; an ozone amount calculating unit receiving a COD value of the wastewater from the COD measuring unit and calculating the amount of ozone associated with a concentration of the organic matter using the COD value; and a controller controlling a production of ozone of an ozone generator based on the amount of ozone calculated by the ozone amount calculating unit.

In addition, the ozone amount calculating unit may calculate the concentration of the organic matter contained in the wastewater through a correlation expression between the measured COD value and the concentration of the organic matter contained in the wastewater, which is previously derived to predict the concentration of the organic matter in the wastewater based on the COD value of the wastewater.

In addition, the correlation expression may calculate the concentration of organic matter in the wastewater by multiplying the COD value by a previously derived correlation ratio.

In addition, the ozone amount calculating unit may calculate the amount of ozone used for decomposing the organic matter contained in the wastewater to a target concentration or less.

In addition, the ozone amount calculating unit may calculate the amount of ozone through an ozone production formula previously derived to calculate the amount of ozone required for decomposition of the organic matter compared with the concentration of the organic matter, the ozone production formula calculating the amount of ozone compared with the calculated concentration of the organic matter.

In addition, the ozone production formula may calculate the amount of ozone required for decomposition of the organic matter contained in the wastewater by multiplying the calculated concentration of the organic matter by a comparison value of the amount of ozone required for decomposition of the organic matter contained in the wastewater to a target concentration with respect to the concentration of the organic matter.

In addition, the ozone amount calculating unit may add a margin from the amount of ozone calculated through the ozone production formula.

Advantageous Effects

According to the wastewater treatment method and system of the present invention, since the production of ozone is adjusted to be associated with a load of organic matter in wastewater to be oxidized, the wastewater may be economically treated and an environmental pollution that may be caused by excess ozone not used for oxidation of the organic matter may be prevented.

In addition, according to the wastewater treatment method and system of the present invention, wastewater may be stably treated so that a concentration of organic matter in treated water obtained by decomposing the organic matter in the wastewater by ozone whose production is adjusted in association with a load of the organic matter in the wastewater is about 1 ppm or less.

BRIEF DESCRIPTION OF THE DRAWINGS

FIG. 1 is a flowchart of a wastewater treatment method according to an embodiment of the present invention.

FIG. 2 is a graph showing a correlation between a chemical oxygen demand (COD) value and a concentration of organic matter according to an embodiment of the present invention.

FIG. 3 is a graph showing results of an experiment to evaluate the amount of ozone required to decompose organic matter of a certain concentration.

FIG. 4 is a block diagram of a wastewater treatment system according to an embodiment of the present invention.

DESCRIPTION OF THE INVENTION

Hereinafter, embodiments of the present invention will be described in detail with reference to the accompanying drawings.

FIG. 1 is a flowchart of a wastewater treatment method according to an embodiment of the present invention.

Referring to FIG. 1, a wastewater treatment method according to an embodiment of the present invention includes measuring a chemical oxygen demand (COD) of wastewater (S10), calculating the amount of ozone required for decomposition of organic matter, controlling a production of ozone with the calculated amount of ozone, and injecting the produced ozone into wastewater. According to the wastewater treatment method, a load of organic matter in wastewater is predicted through measurement of the COD of the wastewater, and ozone is injected into the wastewater by associating the production of ozone with the load of the organic matter in the wastewater, thereby treating the wastewater so that the organic matter therein is decomposed.

In an embodiment, the wastewater treated by the wastewater treatment method according to the present invention may mainly contain phenol produced in a fluidized catalytic cracking (FCC) process that converts heavy crude oil into lighter oil such as gasoline and diesel. In other words, phenol is produced by oil introduced into the FCC process and oxygen input during the process. Phenol, an organic compound in which one hydrogen atom of benzene and a hydroxyl group (—OH) are substituted, is a poisonous substance that may lead to serious disability or death if absorbed into the human body through the digestive system, breathing, or skin contact, is classified as a material contaminating water quality and is subject to domestic emission regulations. For decomposition of phenol, wet peroxidation, catalytic wet air oxidation, adsorption and ozone oxidation reactions are used.

In the wastewater treatment method according to the present invention, ozone is used as an oxidizing agent for decomposing organic matter in wastewater. Ozone is an oxidizing agent having the second strongest oxidizing power among substances on the Earth and is used for decomposing pesticides, removing heavy metals, and decomposing organic matter. Ozone is easily decomposed into oxygen within 2 to 20 hours in the air and within 15 to 30 minutes in water and thus cannot be stored, and when decomposed, ozone is converted to oxygen and is evaluated as an eco-friendly technology.

In operation S10, as a method of indirectly measuring a load of organic matter in the wastewater, the COD of the wastewater is measured. The COD of wastewater needs to be measured in real time because the concentration of organic matter in the treated wastewater may fluctuate in real time. In the present invention, COD of wastewater may be measured in real time and uses a sensor controlled to measure at a regular cycle. As an example, the COD measurement sensor may be s::can's spectro::lyser V3, which may analyze water quality within 1 to 2 minutes.

In operation S10, for the COD measurement of wastewater, a COD of wastewater flowing into a reactor through a pump is measured through a sensor in real time. The sensor is controlled to measure the COD of the wastewater before being injected into the reactor in a unit of measurement equal to a period for controlling the production of ozone using the measured COD value.

In operation S20, the amount of ozone used for decomposition of organic matter contained in the wastewater is calculated using the COD value of the wastewater measured in operation S10. Operation S20 may include calculating a concentration of the organic matter (S21), calculating the amount of ozone (S22), and adding a margin to the calculated amount of ozone (S23) in order to associate an emission rate of ozone with the load of organic matter in the wastewater.

In operation S21, a concentration of organic matter contained in the wastewater is calculated using the COD value of the wastewater measured in operation S10. As in the above example, when the organic matter contained in wastewater corresponds to phenol, a concentration of phenol in the wastewater may be indirectly measured by measuring the COD, which is used as an indicator of water quality, because phenol is an organic matter including carbon, hydrogen, and oxygen.

FIG. 2 is a graph showing a correlation between a COD value and a concentration of organic matter according to an embodiment of the present invention, and is a graph obtained by experimentally measuring a concentration of an organic matter, i.e., phenol, of the corresponding wastewater of which COD is measured, and COD of the wastewater.

Referring to FIG. 2, when the measured value of the concentration of phenol in the wastewater is compared with the measured COD value of the wastewater, it can be seen that there is a relatively high correlation ($R^2=0.9309$) with each other and a concentration of phenol in the wastewater corresponds to a value obtained by multiplying the COD value of the wastewater by a certain proportional constant. Based on the graph, a correlation expression is derived between the concentration of phenol in the wastewater and the COD value of the wastewater: (concentration of phenol)=0.2373×(COD value). The graph and correlation expression are derived for wastewater containing phenol generated in the FCC process but are not limited thereto, and a correlation expression of (concentration of organic matter)=(correlation ratio between COD value and concentration of organic matter)×(COD value) may be applied to calculate the concentration of organic matter based on COD measurement for wastewater containing organic matter.

TABLE 1

| COD (ppm) | Experimental value of concentration of phenol (ppm) | Estimated value of concentration of phenol (ppm) | Experimental value − Estimated value (ppm) | Error rate (%) |
|---|---|---|---|---|
| 180.8 | 45 | 42.90 | 2.10 | 4.67 |
| 171.0 | 44 | 40.58 | 3.42 | 7.78 |
| 170.0 | 44 | 40.34 | 3.66 | 8.32 |
| 160.0 | 41 | 37.97 | 3.03 | 7.40 |
| 179.0 | 45 | 42.48 | 2.52 | 5.61 |
| 191.6 | 45 | 45.46 | −0.46 | 1.02 |
| 199.1 | 44 | 47.25 | −3.25 | 7.39 |
| 171.0 | 43 | 40.58 | 2.42 | 5.63 |
| 169.0 | 43 | 40.10 | 2.90 | 6.74 |

Table 1 shows a COD value, an actually measured experimental value of a concentration of phenol in the wastewater, an estimated value of concentration of phenol predicted with the COD value of the wastewater through a correlation expression derived from the graph, a difference between the experimental value and the estimated value of concentration of phenol, and an error rate between the experimental value and the estimated value.

Referring to Table 1, compared with experimental values obtained by experimentally measuring concentration of organic matter of wastewater, an average error rate of the estimated values of the concentrations of the phenol obtained by substituting measured CODs of wastewater to previously derived correlation expression is about 6.06%, a maximum error rate thereof is 8.32%, and a minimum error rate thereof 1.02%, and thus, it can be seen that the concentration of phenol predicted based on the previously derived correlation expression relatively accurately reflects the actual concentration of phenol in the wastewater.

Based on the verification between the estimated value and the experimental value of the concentration of the organic matter as described above, in the wastewater treatment method according to the present invention, in order to associate the production of ozone with a load of the organic matter in wastewater, the concentration of the organic matter in the wastewater is calculated through a predictive formula for the concentration of the organic matter based on the COD value measured in real time, that is, the correlation expression between the COD value and the concentration of the organic matter, thereby measuring the concentration of the organic matter in the wastewater in real time.

In operation S21, a previously derived correlation expression is used to predict the concentration of organic matter in wastewater based on the measured COD value. By substituting the COD value measured in operation S10 into the correlation expression, the concentration of organic matter contained in the wastewater is calculated. The correlation expression for calculating the concentration of organic matter is a predictive formula for the concentration of organic matter based on the measured COD value of the wastewater, which is a product of the COD value and the correlation ratio. The correlation ratio of the correlation expression may have different values depending on the type of organic matter contained in the wastewater.

In operation S22, the amount of ozone used for decomposing organic matter contained in wastewater to a target concentration or less is calculated using the concentration of organic matter calculated in operation S21. In this case, preferably, the target concentration is at least 1 ppm or less, more preferably, at least 0.5 ppm or less.

In operation S22, a previously derived ozone production formula is used to calculate the amount of ozone associated with the concentration of organic matter in wastewater using the concentration of organic matter calculated in operation S21 to calculate the amount of ozone used to decompose organic matter.

Hereinafter, a process of deriving the ozone production formula is described.

FIG. 3 is a graph showing the results of an experiment to evaluate the amount of ozone required to decompose organic matter of a certain concentration, and the graph of FIG. 3 shows the progress of the concentration of phenol over the injection amount of ozone, while injecting ozone into wastewater to decompose about 100 ppm of phenol contained in the wastewater. Table 2 below shows the injection amount of ozone, the concentration of phenol over the injection amount of ozone, and the injection amount of ozone to the concentration of phenol.

TABLE 2

| Injection amount of ozone (ppm) | Concentration of phenol (ppm) | Injection amount of ozone/concentration of phenol |
|---|---|---|
| 0 | 98.5 | 0 |
| 202 | 8.5 | 2.1 |
| 281 | 1.1 | 2.9 |
| 348 | 0.5 | 3.5 |
| 420 | 0.2 | 4.3 |
| 501 | 0 | 5.1 |
| 524 | 0 | 5.3 |

Referring to FIG. 3 and Table 2, it can be seen that ozone of about 3.1 to 5 times the concentration of phenol is required to decompose the concentration of phenol to 1 ppm or less. The amount of ozone required to decompose the concentration of phenol in wastewater to a target concentration of organic matter, for example, 1 ppm or less, is at least 3.1 times more than that of phenol and ranges from about 3.1 to 5 times that of phenol. A contrast value of the amount of ozone required for the decomposition of phenol to the concentration of phenol is selected in the range of about 3.1 to 5 times in consideration of the target concentration and economic feasibility.

The amount of ozone (unit: ppm) calculated in operation S22 is calculated as a product of the concentration of phenol and the contrast value selected in the range of about 3.1 to about 5 times. That is, the ozone production formula calculates the amount of ozone used to decompose the amount of phenol corresponding to the concentration of phenol calculated in operation S21, which appears as (amount of ozone)=(calculated concentration of phenol)×(contrast value of amount of ozone required to decompose phenol in wastewater to target concentration for concentration of phenol).

As described above, the ozone production formula derived by applying organic matter contained in wastewater to phenol may be generalized even when general organic matter is contained in wastewater. Therefore, in the wastewater treatment method according to the present invention, the amount of ozone required to decompose organic matter contained in wastewater is calculated through an ozone production formula of multiplying the concentration of organic matter calculated to calculate the amount of ozone associated with a load of organic matter in wastewater by a contrast value of the amount of ozone required to decompose the organic matter contained in wastewater having the calculated concentration of organic matter to a target concentration, that is, (amount of ozone)=(calculated concentration of organic matter)×(contrast value of amount of ozone required to decompose organic matter in wastewater to target concentration for the concentration of organic matter).

In operation S22, the ozone production formula previously derived through the derivation process described above is used to calculate the amount of ozone used to decompose organic matter. At this time, in the ozone production formula, the contrast value corresponds to a value previously selected to reduce the concentration of organic matter to a target concentration within a range experimentally derived according to the type of organic matter contained in the wastewater to be treated, and the concentration of the organic matter is a value calculated through the previously derived correlation expression ((concentration of organic matter)=(correlation ratio between COD value and concentration of organic matter)×(COD value)).

Therefore, when the ozone production formula is expressed again, the ozone production formula is (amount of ozone)=(correlation ratio between COD value and concentration of organic matter)×(COD value)×(amount of ozone required to decompose organic matter in wastewater to a target concentration contrast value for the concentration of organic matter). At this time, the unit of the amount of ozone calculated by the ozone production formula is ppm.

In addition, a total production of ozone to be generated by the ozone generator may be obtained by multiplying the amount of ozone calculated by the ozone production formula by a total amount of wastewater to be treated with ozone. Accordingly, the total production of ozone associated with the load of the total organic matter included in the wastewater to be treated is obtained, and it is possible to minimize creation of surplus ozone not used for decomposition of organic matter in the wastewater.

In operation S23, a margin is added to the amount of ozone calculated in operation S22. By adding the margin in this operation, the calculated amount of ozone is modified to slightly increase. The amount of ozone increased by the margin is associated with the concentration of the organic matter in wastewater and ensures a stable organic matter decomposition reaction to lower the concentration of organic matter in the wastewater even when the concentration of organic matter varies over time.

In operation S23, a method of adding a margin may include, for example, a method of selecting and multiplying one of the rational numbers greater than 1 in the derived ozone production formula and a method of adding a predetermined margin amount to the derived ozone production formula.

In operation S30, the production of ozone of the ozone generator is controlled based on the amount of ozone calculated in operation S20. The amount of production of ozone of the ozone generator is adjusted to minimize an occurrence of surplus ozone that does not participate in an organic decomposition reaction.

In operation S30, a total production of ozone to be produced by the ozone generator is calculated as a product of the amount of ozone calculated in operation S20 by a total amount of wastewater to be ozone-treated, and information on the calculated total production of ozone is transmitted to the ozone generator so that the ozone generator is automated to produce an amount of ozone associated with an organic load in the wastewater.

In operation S40, ozone produced by the ozone generator is injected into a reactor in which the wastewater is collected. The injected ozone is used to decompose organic matter in the wastewater, and the surplus ozone that does not participate in the reaction is minimized.

TABLE 3

| COD (ppm) | Concentration of phenol of treated water (ppm) | Actual production of ozone ① (g/hr) | Calculated production of ozone ② (g/hr) | ① − ② | Error rate (%) |
|---|---|---|---|---|---|
| 180.78 | 0.7 | 148.51 | 150.1 | −1.63 | −1.1 |
| 171.33 | 0.7 | 140.40 | 142.3 | −1.89 | −1.3 |
| 191.56 | 0.6 | 155.00 | 159.1 | −4.10 | −2.6 |

Table 3 shows a COD value of wastewater, a concentration of phenol of treated water which is wastewater after being treated by the wastewater treatment method according to an embodiment of the present invention, a production of ozone actually produced by the ozone generator whose production amount is adjusted by the wastewater treatment method according to an embodiment of the present invention, a production of ozone calculated by the wastewater treatment method according to an embodiment of the present invention, a difference between the production amount of actually produced ozone and the calculated production of ozone, and an error rate between the production amount of actually produced ozone and the calculated production of ozone.

It can be seen that, in organic matter of treated water corresponding to wastewater after being treated by the wastewater treatment method according to an embodiment of the present invention, phenol according to an example was entirely treated to a target concentration of 1 ppm or less and the ozone generator whose production amount is adjusted by the wastewater treatment method according to an embodiment of the present invention is stably adjusted in automatic production with a small error rate of 2.6% from the calculated production of ozone.

Hereinafter, the wastewater treatment method according to the present invention is executed by an automated wastewater treatment system, and in the description of the wastewater treatment system according to the present invention, the content overlapping with the content described above in the method will be omitted.

FIG. 4 is a block diagram of a wastewater treatment system according to an embodiment of the present invention.

Referring to FIG. 4, a wastewater treatment system 100 according to an embodiment of the present invention includes a COD measuring unit 110, an ozone amount calculating unit 120, and a controller 130, and automatically adjusts a production of ozone in association with an organic load in wastewater A.

In an embodiment, the COD measuring unit 110 measures a COD of the wastewater A in real time in order to indirectly measure a concentration of organic matter in the wastewater A. The COD measuring unit 110 includes a sensor capable of measuring the COD of the wastewater A in real time, and controls the sensor to measure the COD at a constant cycle. As an example, the COD measurement sensor is s::can's spectro::lyser V3, which may analyze water quality within 1 to 2 minutes.

In the illustrated embodiment, the COD measuring unit 110 measures wastewater flowing through a wastewater pipe 154 or the wastewater A flowing into a reactor 151 through a pump 152 in real time by a sensor. The sensor is controlled to measure a COD of the wastewater A before being injected into the reactor 151 in a unit of a measurement cycle equal to a cycle for controlling the production of ozone using the measured COD value according to the present invention.

The ozone amount calculating unit 120 receives the COD value of the wastewater A from the COD measuring unit 110 and calculates the amount of ozone associated with the concentration of organic matter in the wastewater using the COD value. The ozone amount calculating unit 120 first calculates a concentration of organic matter contained in the wastewater using the COD value of the wastewater. When calculating the concentration of organic matter in the wastewater, the ozone amount calculating unit 120 uses a correlation ratio between a COD of the wastewater required to be treated, a COD of wastewater previously derived through an experiment of measuring a concentration of the organic matter in the wastewater, and a concentration of the organic matter in the wastewater. That is, the ozone amount calculating unit 120 calculates the concentration of the organic matter in the wastewater using the correlation expression between the COD of the wastewater and the concentration of the organic matter in the wastewater and the COD value of the wastewater A received from the COD measuring unit 110.

The correlation expression used by the ozone amount calculating unit 120 to calculate the concentration of organic matter is (concentration of organic matter)=(correlation ratio between COD value and concentration of organic matter)×(COD value), and the correlation ratio is previously derived from treated wastewater and stored in a memory, etc., so as to be used by the ozone amount calculating unit to calculate the concentration of the organic matter.

The ozone amount calculating unit 120 calculates the amount of ozone used to decompose organic matter contained in wastewater to a target concentration or less using the calculated concentration of the organic matter. The ozone amount calculating unit 120 uses a contrast value of the amount of ozone required to decompose the organic matter in the wastewater previously derived by an experiment or the like to a target concentration in order to calculate the amount of ozone. The process of deriving the contrast value has been described above and is pre-stored in a memory or the like, like the correlation ratio.

The ozone amount calculating unit 120 uses an ozone production formula using the contrast value to calculate the amount of ozone associated with the concentration of the organic matter in the wastewater. The ozone production formula is an expression obtained by multiplying the calculated concentration of the organic matter by the contrast value of the amount of ozone required to decompose the organic matter contained in the wastewater to a target concentration for the concentration of the organic matter, that is, (amount of ozone)=(calculated concentration of organic matter)×(contrast value of the amount of ozone required to decompose organic matter in wastewater to a target concentration with respect to the concentration of organic matter).

In the ozone production formula, the concentration of organic matter may be expressed as (correlation ratio between the COD value and the concentration of organic matter)×(COD value), and in other words, the ozone production formula is (amount of ozone)=(correlation ratio between COD value and concentration of organic matter))×(COD value)×(contrast value of the amount of ozone required to decompose organic matter in wastewater to a target concentration with respect to the concentration of organic matter). At this time, a unit of the amount of ozone calculated by the ozone production formula is ppm.

As a result, the ozone amount estimating unit 120 calculates the amount of ozone associated with the correlation ratio between the previously derived COD value and the concentration of organic matter, the contrast value of the amount of ozone required to decompose the organic matter in the wastewater to a target concentration for the concentration of the organic matter, and the concentration of organic matter in wastewater using the measured COD value.

The controller 130 receives information on the calculated amount of ozone from the ozone amount calculating unit 120 and controls the production of ozone of the ozone generator based on the calculated amount of ozone. The controller 130 adjusts the production of ozone of the ozone generator in order to minimize an occurrence of surplus ozone not participating in the organic matter decomposition reaction. A total production of ozone to be produced by the ozone generator 140 is calculated as a product of the calculated amount of ozone and the total amount of wastewater to be treated with ozone, and information on the calculated total production of ozone is transmitted to the ozone generator, so that the ozone generator 140 is automated to product the amount of ozone associated with the load of the organic matter in the wastewater.

The ozone produced by the ozone generator 140 is injected into the reactor 151 in which the wastewater A is collected through the ozone injector 153 and the ozone injection pipe 155. The injected ozone is used to decompose the organic matter in the wastewater, an oxidation-treated water B contains organic matter below the target concentration of 0 to 1 ppm, and the surplus amount of ozone not participating in the reaction is minimized.

Although the present invention has been shown and described with respect to specific embodiments, it will be apparent to those having ordinary skill in the art that the present invention may be variously modified and altered without departing from the spirit and scope of the present invention as defined by the following claims.

DESCRIPTION OF REFERENCE NUMERALS

100: Wastewater treatment system
110: COD measuring unit
120: Ozone amount calculating unit
130: Controller
140: Ozone generator

The invention claimed is:

1. A wastewater treatment method comprising:
measuring a chemical oxygen demand (COD) of wastewater containing organic matter in real time;
calculating an amount of ozone associated with a concentration of the organic matter using the measured COD value; and
controlling a production of ozone of an ozone generator based on the calculated amount of ozone,
wherein the calculating of the amount of ozone comprises calculating the concentration of the organic matter contained in the wastewater through a correlation expression between the measured COD value and the concentration of the organic matter contained in the wastewater, which is previously derived to predict the concentration of the organic matter in the wastewater based on the COD value of the wastewater.

2. The wastewater treatment method of claim 1, wherein the correlation expression calculates the concentration of organic matter in the wastewater by multiplying the COD value by a previously derived correlation ratio.

3. The wastewater treatment method of claim 1, wherein in the calculating of the amount of ozone, the amount of ozone used for decomposing the organic matter contained in the wastewater to a target concentration or less is calculated.

4. The wastewater treatment method of claim 3, wherein the calculating of the amount of ozone further comprises calculating the amount of ozone through an ozone production formula previously derived to calculate the amount of ozone required for decomposition of the organic matter compared with the concentration of the organic matter, the ozone production formula calculating the amount of ozone compared with the concentration of the organic matter calculated in the calculating of the concentration of the organic matter contained in the wastewater.

5. The wastewater treatment method of claim 4, wherein the ozone production formula calculates the amount of ozone required for decomposition of the organic matter contained in the wastewater by multiplying the calculated concentration of the organic matter by a comparison value of the amount of ozone required for decomposition of the organic matter contained in the wastewater to a target concentration with respect to the concentration of the organic matter.

6. The wastewater treatment method of claim 4, wherein the calculating of the amount of ozone further comprises adding a margin from the amount of ozone calculated through the ozone production formula.

7. A wastewater treatment system comprising:
a chemical oxygen demand (COD) measuring unit measuring a COD of wastewater containing organic matter in real time;
an ozone amount calculating unit receiving a COD value of the wastewater from the COD measuring unit and calculating an amount of ozone associated with a concentration of the organic matter using the COD value; and
a controller controlling a production of ozone of an ozone generator based on the amount of ozone calculated by the ozone amount calculating unit,
wherein the ozone amount calculating unit calculates the concentration of the organic matter contained in the wastewater through a correlation expression between the measured COD value and the concentration of the organic matter contained in the wastewater, which is previously derived to predict the concentration of the organic matter in the wastewater based on the COD value of the wastewater.

8. The wastewater treatment system of claim 7, wherein the correlation expression calculates the concentration of organic matter in the wastewater by multiplying the COD value by a previously derived correlation ratio.

9. The wastewater treatment system of claim 7, wherein the ozone amount calculating unit calculates the amount of ozone used for decomposing the organic matter contained in the wastewater to a target concentration or less.

10. The wastewater treatment system of claim 9, wherein the ozone amount calculating unit calculates the amount of ozone through an ozone production formula previously derived to calculate the amount of ozone required for decomposition of the organic matter compared with the concentration of the organic matter, the ozone production formula calculating the amount of ozone compared with the calculated concentration of the organic matter.

11. The wastewater treatment system of claim 10, wherein the ozone production formula calculates the amount of ozone required for decomposition of the organic matter contained in the wastewater by multiplying the calculated concentration of the organic matter by a comparison value of the amount of ozone required for decomposition of the organic matter contained in the wastewater to a target concentration with respect to the concentration of the organic matter.

12. The wastewater treatment system of claim 10, wherein the ozone amount calculating unit adds a margin from the amount of ozone calculated through the ozone production formula.

* * * * *